United States Patent
Ohno et al.

(10) Patent No.: US 8,258,352 B2
(45) Date of Patent: *Sep. 4, 2012

(54) PRODUCTION PROCESS FOR CHLORINE-CONTAINING FLUORINE-CONTAINING COMPOUND

(75) Inventors: Hiromoto Ohno, Minato-ku (JP); Toshio Ohi, Minato-ku (JP); Takami Ohe, Minato-ku (JP)

(73) Assignee: Showa Denko K.K., Tokyo (JP)

( * ) Notice: Subject to any disclaimer, the term of this patent is extended or adjusted under 35 U.S.C. 154(b) by 417 days.

This patent is subject to a terminal disclaimer.

(21) Appl. No.: 12/593,754

(22) PCT Filed: Mar. 27, 2008

(86) PCT No.: PCT/JP2008/055821
§ 371 (c)(1),
(2), (4) Date: Sep. 29, 2009

(87) PCT Pub. No.: WO2008/120652
PCT Pub. Date: Oct. 9, 2008

(65) Prior Publication Data
US 2010/0105968 A1 Apr. 29, 2010

(30) Foreign Application Priority Data
Mar. 30, 2007 (JP) .................. 2007-093945

(51) Int. Cl.
*C07C 17/00* (2006.01)
(52) U.S. Cl. ....................................... 570/161
(58) Field of Classification Search .................. 570/161
See application file for complete search history.

(56) References Cited

FOREIGN PATENT DOCUMENTS

| | | |
|---|---|---|
| JP | 64-038034 A | 2/1989 |
| JP | 4-500520 A | 1/1992 |
| JP | 2006-342059 A | 12/2006 |
| WO | 2007/125975 A1 | 11/2007 |

OTHER PUBLICATIONS

Computer translation of JP 2006-342059, Dec. 2006.*

* cited by examiner

*Primary Examiner* — Jafar Parsa
(74) *Attorney, Agent, or Firm* — Sughrue Mion, PLLC

(57) ABSTRACT

The production process of the present invention for a chlorine-containing fluorine-containing compound is characterized in that a reaction of adding chlorine atoms to a carbon-carbon unsaturated bond of a hydrogen-containing compound having a carbon-carbon unsaturated bond is carried out under the presence of a fluorine gas. The hydrogen-containing compound having a carbon-carbon unsaturated bond may be 3,4-dichlorobutene-1. Further, the present invention provides a process for producing efficiently and economically 1,2,3,4-tetrachlorohexafluorobutane from 3,4-dichlorobutene-1 described above. According to the present invention, chlorination and fluorination of the hydrogen-containing compound having a carbon-carbon unsaturated bond are carried out in a single step, and therefore a chlorine-containing fluorine-containing compound can be more economically produced at a higher yield than in a conventional process in which two reactions are individually carried out.

8 Claims, No Drawings ial ally at a high yield. Thus, they have come to complete the present invention.

PRODUCTION PROCESS FOR CHLORINE-CONTAINING FLUORINE-CONTAINING COMPOUND

FIELD OF THE INVENTION

The present invention relates to a production process for a chlorine-containing fluorine-containing compound.

More specifically, the present invention relates to a production process for a chlorine-containing fluorine-containing compound such as 1,2,3,4-tetrachlorohexafluorobutane which is useful as a synthetic raw material etc. for hexafluoro-1,3-butadiene attracting attentions as an etching gas etc. for semiconductors.

BACKGROUND OF THE INVENTION 1,2,3,4-Tetrachlorohexafluorobutane in which all of hydrogen atoms bonded to carbon atoms are substituted with chlorine atoms and fluorine atoms is, as described above, a compound which is important as, for example, a synthetic raw material etc. for hexafluoro-1,3-butadiene attracting attentions as a finely processing etching gas for semiconductors.

A process described in the following patent document has so far been known as a production process for 1,2,3,4-tetrachlorohexafluorobutane.

A process for producing 1,2,3,4-tetrachlorohexafluorobutane by reacting a compound represented by $CClX^1X^2$—$CClX^3$—$CClX^4$—$CClX^5X^6$ obtained by reacting, for example, $CX^1X^2$=$CX^3$—$CX^4$=$CX^5X^6$ (X is a hydrogen atom or a fluorine atom) with chlorine, with fluorine in a liquid phase is described in Japanese Patent Application Laid-Open No. 2006-342059 (patent document 1). It is described therein that when 1,2,3,4-tetrachlorohexafluorobutane is used as a common solvent in chlorination reaction and fluorination reaction, an advantage is obtained that it is unnecessary to separate the solvent from the product, so that it is particularly preferred. However, chlorination reaction and fluorination reaction have to be individually carried out in the above reaction. Accordingly, reaction apparatuses and operations for carrying out two processes are required in the process described in the patent document 1, and a problem is involved therein in terms of a cost.

Patent document 1: Japanese Patent Application Laid-Open No. 2006-342059

DISCLOSURE OF THE INVENTION

An object of the present invention is to solve the problem that chlorination reaction and fluorination reaction each have had to be individually carried out when obtaining a chlorine-containing fluorine-containing compound from a hydrogen-containing compound having a carbon-carbon unsaturated bond and to provide a process for industrially producing a chlorine-containing fluorine-containing compound at a high yield.

Further, an object of the present invention is to provide a process for industrially producing 1,2,3,4-tetrachlorohexafluorobutane which is useful as a synthetic raw material etc. for hexafluoro-1,3-butadiene attracting attentions as an etching gas etc. for semiconductors at a high yield.

The present inventors have found a process in which chlorination fluorination reaction (this means chlorination reaction and fluorination reaction; hereinafter the same shall apply) to carry out reaction for adding chlorine atoms to the carbon-carbon unsaturated bond of a hydrogen-containing compound having a carbon-carbon unsaturated bond under the presence of a fluorine gas is carried out to thereby make it possible to carry out reactions which have so far been individually carried out in a single step and in which a chlorine-containing fluorine-containing compound is produced industrially at a high yield. In particular, they have found a process to subject 3,4-dichlorobutene-1 to chlorination fluorination reaction to obtain 1,2,3,4-tetrachlorohexafluorobutane which is a useful chlorine-containing fluorine-containing compound at a high yield. Thus, they have come to complete the present invention.

The present invention relates to the following items [1] to [9].

[1] A production process for a chlorine-containing fluorine-containing compound in which a hydrogen-containing compound having a carbon-carbon unsaturated bond is reacted with a chlorine gas to add chlorine atoms to the carbon-carbon unsaturated bond and in which all of the hydrogen atoms are fluorinated, wherein the reaction of adding the chlorine atoms to the carbon-carbon unsaturated bond is carried out under the presence of a fluorine gas.

[2] The production process for a chlorine-containing fluorine-containing compound as described in the above item [1], wherein the hydrogen-containing compound having a carbon-carbon unsaturated bond is 3,4-dichlorobutene-1.

[3] The production process for a chlorine-containing fluorine-containing compound as described in the above item [1], wherein the reaction is carried out under the presence of a solvent.

[4] The production process for a chlorine-containing fluorine-containing compound as described in the above item [1], wherein a reaction temperature for carrying out the reaction falls in a range of −20° C. to 80° C.

[5] The production process for a chlorine-containing fluorine-containing compound as described in the above item [1], wherein a reaction pressure for carrying out the reaction falls in a range of 0.1 MPa to 2.0 MPa.

[6] The production process for a chlorine-containing fluorine-containing compound as described in the above item [1], wherein the chlorine gas and/or the fluorine gas are diluted with a diluent gas.

[7] The production process for a chlorine-containing fluorine-containing compound as described in the above item [6], wherein the diluent gas is at least one inert gas selected from the group consisting of a nitrogen gas, a helium gas, an argon gas and a neon gas.

[8] The production process for a chlorine-containing fluorine-containing compound as described in the above item [2], wherein the 3,4-dichlorobutene-1 is produced by chlorination reaction of 1,3-butadiene or isomerization reaction of 1,4-dichlorobutene-2.

[9] A production process for 1,2,3,4-tetrachlorohexafluorobutane comprising:
a step of subjecting 3,4-dichlorobutene-1 to chlorination reaction and fluorination reaction, wherein a chlorine gas is fed to 3,4-dichlorobutene-1 under the presence of a fluorine gas to add chlorine atoms to a carbon-carbon unsaturated bond, and a fluorine gas is further fed thereto to substitute all of the hydrogen atoms with fluorine atoms;
a step of separating a product obtained in the foregoing step in a distillation column; and
a step of contacting 1,2,3,4-tetrachlorohexafluorobutane obtained by the distillation with alkali and/or water.

That is, according to the present invention, in producing a chlorine-containing fluorine-containing compound using a hydrogen-containing compound having a carbon-carbon unsaturated bond, reaction for adding chlorine atoms to the carbon-carbon unsaturated bond is carried out under the presence of a fluorine gas, whereby the chlorine-containing fluorine-containing compound can be efficiently and economically obtained. In particular, according to the present invention, 3,4-dichlorobutene-1 is subjected to chlorination fluorination reaction, whereby 1,2,3,4-tetrachlorohexafluorobutane which is a useful chlorine-containing fluorine-containing compound can be efficiently and economically produced.

ADVANTAGES OF THE INVENTION

According to the present invention, a chlorine-containing fluorine-containing compound can be produced in a single step using a hydrogen-containing compound having a carbon-carbon unsaturated bond as a raw material. Therefore, chlorination fluorination reaction can be carried out more efficiently in the present invention than in a conventional process in which two reactions are individually carried out. Accordingly, the present invention is excellent in terms of the yield and the cost. Further, since the reaction is carried out in a single step, the reaction time is shortened as compared with carrying out individually two reactions, and the production facilities can be simplified. Hence, the production process of the present invention is superior in production efficiency to conventional processes.

That is, according to the present invention, a process in which a chlorine-containing fluorine-containing compound is industrially and efficiently produced at a high yield from a hydrogen-containing compound having a carbon-carbon unsaturated bond as a raw material is provided.

PREFERRED EMBODIMENTS OF THE INVENTION

The preferred embodiment of the present invention shall be specifically explained.

The present invention is a process for producing a chlorine-containing fluorine-containing compound in which a hydrogen-containing compound having a carbon-carbon unsaturated bond is reacted with a chlorine gas to add chlorine atoms to the carbon-carbon unsaturated bond and in which all of the hydrogen atoms are fluorinated, wherein a chlorine gas and a fluorine gas are supplied at the same time in carrying out the reaction of adding chlorine atoms to the carbon-carbon unsaturated bond to produce the chlorine-containing fluorine-containing compound.

Carrying out chlorination reaction and fluorination reaction in a single step makes it possible to produce the chlorine-containing fluorine-containing compound more efficiently and more economically than in a conventionally conducted process in which chlorination reaction and fluorination reaction are individually carried out.

The compound used as the raw material in the present invention is a hydrogen-containing unsaturated compound having 3 or more carbon atoms, preferably 3 to 6 carbon atoms. In this connection, the unsaturated compound used as the raw material is a compound having at least one double bond in the molecule, and the unsaturated compound used as the raw material in the present invention is particularly preferably a compound having a double bond at its molecular end. A part of hydrogen atoms in the unsaturated compound may be substituted with a halogen atom such as a chlorine atom.

The unsaturated compound having 3 or more carbon atoms includes, for example, 3,4-dichlorobutene-1 which has 4 carbon atoms and has one double bond at its molecular end and in which two hydrogen atoms are substituted with chlorine atoms. When the unsaturated compound is used as the raw material to carry out the chlorination fluorination reaction of the present invention, chlorine atoms are added to a double bond in the compound, and all of the hydrogen atoms are substituted with fluorine atoms, whereby 1,2,3,4-tetrachlorohexafluorobutane which is an industrially useful chlorine-containing fluorine-containing compound can be obtained.

For example, as shown in the following chemical formula, 3,4-dichlorobutene-1 used above can be obtained as an intermediate in a production stage of a chloroprene rubber which is industrially produced. The Formula (1) shows a principal reaction, and Formula (2) is a formula showing reaction in which 1,4-dichlorobutene-2 produced by side reaction is converted into targeted 3,4-dichlorobutene-1 by isomerization.

[Chem. 1]

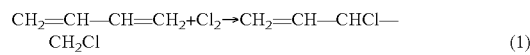

(1)

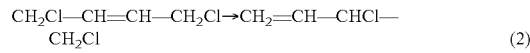

(2)

The unsaturated compound used as the raw material in the present invention is preferably 3,4-dichlorobutene-1 having a double bond at its molecular end, and 1,4-dichlorobutene-2 is preferably used after isomerized to 3,4-dichlorobutene-1 as shown in Formula (2) described above. Usually, a content of 1,4-dichlorobutene-2 is controlled to 10% by mass or less.

When 3,4-dichlorobutene-1 is used as the unsaturated compound in the present invention, a purity thereof is preferably 90 mole % or more, more preferably 95 mole % or more. Controlling a purity of 3,4-dichlorobutene-1 to the above range makes it possible to inhibit generation of by-products and cut down the purifying cost.

In the production process for a chlorine-containing fluorine-containing compound according to the present invention, a chlorine gas and a fluorine gas are supplied at the same time and reacted in carrying out reaction in which chlorine atoms are added to a carbon-carbon unsaturated bond of a hydrogen-containing unsaturated compound having 3 or more carbon atoms. In this respect, carrying out chlorination reaction while supplying a fluorine gas at the same time means that the chlorine gas and the fluorine gas are introduced at the same time into the unsaturated compound which is the raw material to carry out addition reaction of chlorine atoms to a carbon-carbon unsaturated bond and substitution reaction of hydrogen atoms with fluorine atoms in the same reactor. In this case, the chlorine gas and the fluorine gas may be each independently supplied to the reactor or may be supplied in the form of a mixed gas obtained by mixing the chlorine gas and the fluorine gas in a certain proportion in advance.

As a reactor for carrying out the above reaction, for example, a pressure reactor such as an autoclave equipped with, a stirring device, line for blowing gas (a gas phase part and/or a liquid phase part), a temperature controlling device (heating and/or cooling) and a pressure gauge can be used. Parts brought into contact with a liquid phase such as the reactor and the stirring device are liable to be corroded. Therefore, they are preferably formed by inconel, hastelloy (HC) or SUS which are corrosive resistant materials, or they are preferably devices or the like subjected to lining with Teflon (registered trademark). However, nickel which is sometimes contained in corrosive resistant materials is turned into fluoride in a certain case, and nickel fluoride accelerates substitution reaction of Cl with F, so that a material having a low nickel content is preferably used.

The autoclave described above is charged with, for example, 3,4-dichlorobutene-1 as a starting material, and the aforementioned chlorination fluorination reaction is carried out while stirring.

A reaction temperature of the chlorination fluorination reaction is maintained in a temperature range of preferably −20° C. to 80° C., more preferably 0° C. to 60° C. Maintaining the reaction temperature in the range described above allows the reaction to proceed smoothly and inhibits side reactions such as C—C cleavage, excessive chlorination and excessive fluorination, whereby the chlorine-containing fluorine-containing compound can be obtained at a good yield. In this case, provided the starting material is 3,4-dichlorobutene-1, 1,2,3,4-tetrachlorohexafluorobutane can be obtained.

A reaction pressure for carrying out the reaction described above falls in a range of preferably 0.1 MPa to 2.0 MPa, more preferably 0.1 MPa to 1.0 MPa. Setting the reaction pressure to the above range allows the reaction to proceed smoothly and does not require a reactor having a strong pressure resistant structure. Therefore, the reaction is carried out preferably at the reaction pressure described above from an economical standpoint of view.

The chlorine gas and the fluorine gas introduced into the reactor maintained at the aforementioned temperature and the pressure are preferably a chlorine gas diluted with a diluent gas and a fluorine gas diluted with a diluent gas. The diluted chlorine gas and diluted fluorine gas can be each individually introduced into the reactor from the liquid phase part or can be introduced as well in the form of a mixed gas obtained by mixing the chlorine gas and the fluorine gas in a step before introducing the gases into the reactor. The mixed gas of the chlorine gas and the fluorine gas can be introduced into the liquid phase part of the reactor or can be introduced as well into the gas phase part thereof.

A concentration of the introduced chlorine gas is preferably 70% by volume or more, more preferably 90 to 100% by volume. Controlling the concentration of the chlorine gas within the above range makes it possible to shorten the reaction time, and it is economical to carry out the reaction at the chlorine gas concentration described above.

On the other hand, a concentration of the introduced fluorine gas is preferably 20% by volume or more, more preferably 40 to 70% by volume. Controlling the concentration of the fluorine gas within the above range makes it possible to shorten the reaction time, and it is economical to carry out the reaction at the fluorine gas concentration described above.

In the present invention, a gas inert to the raw materials, the chlorine gas, the fluorine gas and the reaction product such as a nitrogen gas, a helium gas, an argon gas and a neon gas can be used as the diluent gas for diluting the chlorine gas and the fluorine gas. They can be used alone or in combination thereof. Among the above diluent gases, a nitrogen gas which is the most inexpensive is preferred.

The reaction time in these conditions is usually 20 to 100 hours, preferably 20 to 72 hours.

The reaction can be carried out by either a batch type or a flowing type.

As described above, the production process for a chlorine-containing fluorine-containing compound of the present invention can be carried out without using particularly a reaction solvent, but it can be carried out as well using a reaction solvent as shown below.

The production process for a chlorine-containing fluorine-containing compound of the present invention can be used preferably as a process in which a chlorine gas and a fluorine gas are supplied to 3,4-dichlorobutene-1 at the same time under the presence of a solvent to carry out a chlorination fluorination reaction to thereby produce 1,2,3,4-tetrachlorohexafluorobutane.

Similarly to the case described above, as the reactor, for example, a pressure reactor such as an autoclave equipped with a stirring device, line for blowing a gas (a gas phase part and/or a liquid phase part), a temperature controlling device (heating and/or cooling), a pressure gauge and the like can be used.

In the present invention, a solvent is introduced into a pressure resistant reactor formed by the corrosive resistant material described above.

The solvent which can be used in the present invention is preferably chlorocarbons, chlorofluorocarbons, perfluorocarbons and hydrogen fluoride. Carbon tetrachloride, trichlorotrifluoroethane and the like can be shown as the examples of the chlorocarbons and the chlorofluorocarbons.

Thus, in a compound in which all hydrogen atoms bonded to carbon atoms are substituted with halogen atoms such as a chlorine atom and a fluorine atom, substitution reaction is less liable to proceed even if brought into contact with a chlorine gas and a fluorine gas, and the chlorine-containing fluorine-containing compound which is the targeted compound in the production process of the present invention can be efficiently produced.

A concentration of 3,4-dichlorobutene-1 which is the raw material added to the solvent is preferably 10% by mass or more, more preferably 30 to 95% by mass. Provided the concentration of 3,4-dichlorobutene-1 added to the solvent is low, a volume of the reactor is increased, and therefore the concentration of 3,4-dichlorobutene-1 is preferably high from an economical viewpoint.

The reactor is charged with 3,4-dichlorobutene-1 and the solvent, and the reaction is carried out while stirring.

Because of the same reason as described above, the reaction temperature falls in a range of preferably −20° C. to 80° C., more preferably 0° C. to 60° C.

Because of the same reason as described above, the reaction pressure falls as well in a range of preferably 0.1 MPa to 2.0 MPa, more preferably 0.1 MPa to 1.0 MPa.

A chlorine gas and a fluorine gas introduced into the reactor maintained at the above temperature and the pressure are preferably a chlorine gas diluted with a diluent gas and a fluorine gas diluted with a diluent gas. The diluted chlorine gas and the diluted fluorine gas can be each individually introduced into the reactor from the liquid phase part or can be introduced as well in the form of a mixed gas obtained by mixing the chlorine gas and the fluorine gas in a step before introducing the gases into the reactor. The mixed gas of the chlorine gas and the fluorine gas can be introduced into the liquid phase part of the reactor or can be introduced as well into the gas phase part thereof.

Because of the same reason as described above, a concentration of the introduced chlorine gas is preferably 70% by volume or more, more preferably 90 to 100% by volume.

Further, because of the same reason as described above, a concentration of the introduced fluorine gas is preferably 20% by volume or more, more preferably 40 to 70% by volume. Controlling the concentrations of the chlorine gas and the fluorine gas within the above ranges makes it possible to shorten the reaction time, and it is economical to carry out the reaction at the above chlorine gas concentration and the above fluorine gas concentration.

In the present invention, a gas inert to the raw materials, the chlorine gas, the fluorine gas and the reaction product such as a nitrogen gas, a helium gas, an argon gas and a neon gas can be used as the diluent gas for diluting the chlorine gas and the fluorine gas. They can be used alone or in combination thereof. Among the above diluent gases, a nitrogen gas which is the most inexpensive is preferred.

The reaction time in these conditions is usually 20 to 100 hours, preferably 20 to 72 hours.

The reaction can be carried out by either a batch type or a flowing type.

3,4-Dichlorobutene-1 is chlorinated and fluorinated by carrying out the reaction in the manner described above, and at least a part thereof is converted to 1,2,3,4-tetrachlorohexafluorobutane which is a chlorine-containing fluorine-containing compound. A large part of the 1,2,3,4-tetrachlorohexafluorobutane is present in a state of being dissolved in the reaction solvent, and therefore the reaction solvent, 3,4-dichlorobutene-1 used as the raw material, 1,2,3,4-tetrachlorohexafluorobutane produced by the reaction and side reaction products are contained in the reaction liquid obtained after carrying out the reaction in the manner described above.

In the production process for 1,2,3,4-tetrachlorohexafluorobutane according to the present invention, distillation is carried out by using at least one distillation column, preferably two or more distillation columns in order to separate 1,2,3,4-tetrachlorohexafluorobutane from the reaction liquid.

The reaction liquid is introduced into the first distillation column by, for example, a pump and is separated into low boiling matters and high boiling matters. Since 1,2,3,4-tetrachlorohexafluorobutane which is the targeted product is contained in the low boiling matters, the low boiling matters removed from the first distillation column described above are further introduced, if necessary, into the second distillation column and distilled to remove impurities contained in 1,2,3,4-tetrachlorohexafluorobutane. Further, if necessary, the same operation is repeated in the third and fourth distillation columns.

A fluorine gas and the like are mixed in 1,2,3,4-tetrachlorohexafluorobutane thus obtained by distillation in a certain case, and therefore the 1,2,3,4-tetrachlorohexafluorobutane is brought into contact with an alkaline substance and/or water to transfer water-soluble components such as the fluorine gas contained in the 1,2,3,4-tetrachlorohexafluorobutane into the aqueous phase or to neutralize them. When hydrogen fluoride is used as the solvent, hydrogen fluoride can also be transferred into the aqueous phase or neutralized.

The examples of the alkaline substance used in the present invention include alkali metal compounds such as sodium hydroxide, potassium hydroxide and lithium hydroxide and alkaline earth metal compounds such as calcium hydroxide. The above alkaline substances are usually used in a state of being dissolved or dispersed in water.

By bringing water containing the above alkaline substance into contact with 1,2,3,4-tetrachlorohexafluorobutane, acidic components such as a fluorine gas form salts and are transferred into the aqueous phase. Accordingly, 1,2,3,4-tetrachlorohexafluorobutane can be refined by separating water brought into contact with 1,2,3,4-tetrachlorohexafluorobutane in the above manner. The operation described above can be repeatedly carried out. When hydrogen fluoride is used as the solvent, hydrogen fluoride is also transferred into the aqueous phase, and therefore hydrogen fluoride can be removed.

When 1,2,3,4-tetrachlorohexafluorobutane is brought into contact with water containing the alkaline substance or water in the manner described above, a part of water is dissolved in 1,2,3,4-tetrachlorohexafluorobutane in a certain case. Therefore, 1,2,3,4-tetrachlorohexafluorobutane brought into contact with water in the manner described above is preferably brought into contact with a porous refining material to remove moisture contained in 1,2,3,4-tetrachlorohexafluorobutane by adsorbing it on the porous refining material.

Carbonaceous solid materials, alumina, zeolite and the like can be listed as the examples of the porous refining materials used in the above case. In the present invention, molecular sieves 3A, 4A and 5A are particularly preferably used. Contact with the above porous refining material can be repeatedly carried out. Temperature in the contact step is preferably in a range of 10° C. to 60° C.

A yield of 1,2,3,4-tetrachlorohexafluorobutane based on the starting raw material is usually 60 mole % or more, and 1,2,3,4-tetrachlorohexafluorobutane having a high purity can be very efficiently obtained.

EXAMPLES

The present invention shall be explained below with reference to examples, but the present invention shall by no means be restricted by the examples.

Raw Material Example

Industrially produced 1,3-butadiene was subjected to chlorination reaction to produce principally 3,4-dichlorobutene-1 and 1,4-dichlorobutene-2. 1,4-Dichlorobutene-2 was converted into 3,4-dichlorobutene-1 by isomerization reaction, and by-products were separated by distillation to obtain 3,4-dichlorobutene-1. The resultant was analyzed by gas chromatography to find that purity of 3,4-dichlorobutene-1 was 99.3 mole %.

Example 1

A SUS 304-made (Teflon (registered trademark) lining) reactor having a content volume of 200 ml was charged with 50 g (0.4 mole) of 3,4-dichlorobutene-1 obtained in the production example of the raw material described above, and a nitrogen gas was introduced thereinto at a pressure of 1.0 MPa to carry out a leaking test. Then, the nitrogen gas was purged, and a temperature in the reactor was maintained at 5° C. while stirring.

Then, a chlorine gas diluted to 95% by volume with a nitrogen gas and a fluorine gas likewise diluted to 60% by volume with a nitrogen gas were mixed in a stage before introduced into the autoclave and the resultant was introduced from a liquid phase part at a pressure of 0.7 MPa through a gas introducing tube mounted in the autoclave to start reaction, and they were reacted for 2 hours. After 2 hours passed, the nitrogen gas which was a diluent gas was principally purged from a gas phase part of the autoclave, and then repeated was an operation in which the mixed gas of the 95 volume % chlorine gas and the 60 volume % fluorine gas was introduced from the liquid phase part at a pressure of 0.7 MPa. Finally, the reaction temperature was elevated up to 40° C. to carry out the reaction only with the 60 volume % fluorine gas, and the reaction was completed.

The introduced chlorine gas was 0.36 mole (0.9 mole times based on 3,4-dichlorobutene-1), and the fluorine gas was 2.4 mole (6 mole times based on 3,4-dichlorobutene-1).

The reaction product was recovered and analyzed by gas chromatography. The analytical result is shown below.

Yield of 1,2,3,4-tetrachlorohexafluorobutane: 72.2%.

As apparent from the result, 1,2,3,4-tetrachlorohexafluorobutane can be produced from 3,4-dichlorobutene-1 at a high yield by supplying a chlorine gas and a fluorine gas at the same time to react them.

Example 2

A SUS 304-made (Teflon (registered trademark) lining) reactor having a content volume of 200 ml was charged with 50 g (0.4 mole) of 3,4-dichlorobutene-1 obtained in the production example of the raw material described above, and a nitrogen gas was introduced thereinto at a pressure of 1.0 MPa to carry out a leaking test. Then, the nitrogen gas was purged, and a temperature in the reactor was maintained at 5° C. while stirring.

Then, a chlorine gas diluted to 95% by volume with a nitrogen gas and a fluorine gas likewise diluted to 60% by volume with a nitrogen gas were mixed in a stage before introduced into the autoclave and the resultant was introduced from a liquid phase part at a pressure of 0.7 MPa through a gas introducing tube mounted in the autoclave to start reaction, and they were reacted for 2 hours. After 2 hours passed, the nitrogen gas which was a diluent gas was principally purged from a gas phase part of the autoclave, and then repeated was an operation in which the mixed gas of the 95 volume % chlorine gas and the 60 volume % fluorine gas was introduced from the liquid phase part at a pressure of 0.7 MPa. Finally, the reaction temperature was elevated up to 40° C. to carry out the reaction only with the 60 volume % fluorine gas, and the reaction was completed.

The introduced chlorine gas was 0.56 mole (1.4 mole times based on 3,4-dichlorobutene-1), and the fluorine gas was 2.4 mole (6 mole times based on 3,4-dichlorobutene-1).

The reaction product was recovered and analyzed by gas chromatography. The analytical result is shown below.

Yield of 1,2,3,4-tetrachlorohexafluorobutane: 42.2%.

This Example 2 was an example in which a supplying amount of the chlorine gas was increased as compared with that in Example 1. Observed was the trend that as the supplying amount of the chlorine gas was increased, a production amount of excessively chlorinated compounds which were by-products, primarily pentachloropentafluorobutane was increased and that the yield of 1,2,3,4-tetrachlorohexafluorobutane which was the targeted product was reduced.

Example 3

A SUS 304-made (Teflon (registered trademark) lining) reactor having a content volume of 200 ml was charged with 50 g of carbon tetrachloride which was a solvent and 50 g (0.4 mole) of 3,4-dichlorobutene-1 obtained in the production example of the raw material described above, and a nitrogen gas was introduced thereinto at a pressure of 1.0 MPa to carry out a leaking test. Then, the nitrogen gas was purged, and a temperature in the reactor was maintained at 5° C. while stirring.

Then, a chlorine gas diluted to 95% by volume with a nitrogen gas and a fluorine gas likewise diluted to 60% by volume with a nitrogen gas were mixed in a stage before introduced into the autoclave and the resultant was introduced from a liquid phase part at a pressure of 0.7 MPa through a gas introducing tube mounted in the autoclave to start reaction, and they were reacted for 2 hours. After 2 hours passed, the nitrogen gas which was a diluent gas was principally purged from a gas phase part of the autoclave, and then repeated was an operation in which the mixed gas of the 95 volume % chlorine gas and the 60 volume % fluorine gas was introduced from the liquid phase part at a pressure of 0.7 MPa. Finally, the reaction temperature was elevated up to 40° C. to carry out the reaction only with the 60 volume % fluorine gas, and the reaction was completed.

The introduced chlorine gas was 0.37 mole (0.925 mole times based on 3,4-dichlorobutene-1), and the fluorine gas was 2.4 mole (6 mole times based on 3,4-dichlorobutene-1). The reaction product containing the solvent was recovered and analyzed by gas chromatography. The analytical result is shown below.

Yield of 1,2,3,4-tetrachlorohexafluorobutane: 75.2%.

As apparent from the result, 1,2,3,4-tetrachlorohexafluorobutane can be produced at a high yield in a single step even under the presence of the solvent.

INDUSTRIAL APPLICABILITY

According to the production process of the present invention for a chlorine-containing fluorine-containing compound, chlorination and fluorination of a hydrogen-containing compound having a carbon-carbon unsaturated bond are carried out in a single step, and therefore a chlorine-containing fluorine-containing compound can be more efficiently and more economically produced than in a conventional process in which chlorination reaction and fluorination reaction are individually carried out. According to the production process of the present invention, for example, 1,2,3,4-tetrachlorohexafluorobutane which is useful as a synthetic raw material and the like for hexafluoro-1,3-butadiene attracting attentions as an etching gas and the like for semiconductors can be industrially produced at a low cost and a high yield.

The invention claimed is:

1. A production process for 1,2,3,4-tetrachlorohexafluorobutane in which 3,4-dichlorobutene-1 is reacted with a chlorine gas to add chlorine atoms to the carbon-carbon unsaturated bond and in which all of the hydrogen atoms are fluorinated, wherein the reaction of adding the chlorine atoms to the carbon-carbon unsaturated bond is carried out under the presence of a fluorine gas, such that the chlorination and the fluorination are carried out in a single step.

2. The production process for 1,2,3,4-tetrachlorohexafluorobutane as described in claim 1, wherein the reaction is carried out under the presence of a solvent.

3. The production process for 1,2,3,4-tetrachlorohexafluorobutane as described in claim 1, wherein a reaction temperature for carrying out the reaction falls in a range of −20° C. to 80° C.

4. The production process for 1,2,3,4-tetrachlorohexafluorobutane as described in claim 1, wherein a reaction pressure for carrying out the reaction falls in a range of 0.1 MPa to 2.0 MPa.

5. The production process for 1,2,3,4-tetrachlorohexafluorobutane as described in claim 1, wherein the chlorine gas and/or the fluorine gas are diluted with a diluent gas.

6. The production process for 1,2,3,4-tetrachlorohexafluorobutane as described in claim 5, wherein the diluent gas described above is at least one inert gas selected from the group consisting of a nitrogen gas, a helium gas, an argon gas and a neon gas.

7. The production process for 1,2,3,4-tetrachlorohexafluorobutane as described in claim 1, wherein the 3,4-dichlorobutene-1 is produced by chlorination reaction of 1,3-butadiene or isomerization reaction of 1,4-dichlorobutene-2.

8. A production process for 1,2,3,4-tetrachlorohexafluorobutane comprising:

a step of subjecting 3,4-dichlorobutene-1 to chlorination reaction and fluorination reaction, wherein a chlorine gas is fed to 3,4-dichlorobutene-1 under the presence of a fluorine gas to add chlorine atoms to a carbon-carbon unsaturated bond, and a fluorine gas is further fed thereto to substitute all of the hydrogen atoms with fluorine atoms;

a step of separating a product obtained in the foregoing step in a distillation column; and a step of contacting 1,2,3,4-tetrachlorohexafluorobutane obtained by the distillation with alkali and/or water.

* * * * *